US012421492B2

(12) United States Patent
Kober et al.

(10) Patent No.: US 12,421,492 B2
(45) Date of Patent: Sep. 23, 2025

(54) CELL CULTURE MEDIUM FOR CULTIVATING CELLS, METHOD FOR CULTIVATING CELLS, AND METHOD FOR EXPRESSING AT LEAST ONE RECOMBINANT PROTEIN IN A CELL CULTURE

(71) Applicant: UGA BIOPHARMA GMBH, Henningsdorf (DE)

(72) Inventors: Lars Kober, Henningsdorf (DE); Sarah Herrmann, Henningsdorf (DE)

(73) Assignee: UGA BIOPHARMA GMBH, Henningsdorf (DE)

( * ) Notice: Subject to any disclaimer, the term of this patent is extended or adjusted under 35 U.S.C. 154(b) by 800 days.

(21) Appl. No.: 17/635,964

(22) PCT Filed: Aug. 14, 2020

(86) PCT No.: PCT/EP2020/072896
§ 371 (c)(1),
(2) Date: Feb. 16, 2022

(87) PCT Pub. No.: WO2021/032637
PCT Pub. Date: Feb. 25, 2021

(65) Prior Publication Data
US 2022/0298472 A1    Sep. 22, 2022

(30) Foreign Application Priority Data
Aug. 16, 2019    (EP) ..................... 19192089

(51) Int. Cl.
*C12N 5/071*    (2010.01)
*C12N 5/00*    (2006.01)
(52) U.S. Cl.
CPC ......... *C12N 5/0602* (2013.01); *C12N 5/0018* (2013.01); *C12N 2500/24* (2013.01); *C12N 2500/32* (2013.01); *C12N 2500/38* (2013.01)
(58) Field of Classification Search
CPC ..................................................... C12N 5/00
See application file for complete search history.

(56) References Cited

U.S. PATENT DOCUMENTS 8,637,312 B2 *    1/2014   Kruger et al. ........... C12N 5/00
                                                      435/405
2012/0021510 A1    1/2012   Hegel et al.

FOREIGN PATENT DOCUMENTS

| CA | 2756247 C    |   | 5/2015  |           |
|----|--------------|---|---------|-----------|
| CN | 101735980    | * | 6/2010  |           |
| CN | 105154396    | * | 12/2015 |           |
| EP | 2 016 940 A1 |   | 1/2009  |           |
| WO | WO 93/00423 A1 | | 1/1993  |           |
| WO | WO 9300423   | * | 1/1993  | C12N 5/00 |
| WO | WO 01/16294 A2 | | 3/2001  |           |
| WO | WO-2009087087 A1 | * | 7/2009 | C12N 5/0037 |
| WO | WO 2012079679 | * | 6/2012 | C12N 5/00 |
| WO | WO 2016/156476 A1 | | 10/2016 |       |
| WO | WO 2018/0249750 | * | 9/2018 |          |

OTHER PUBLICATIONS

Le Zhu et al. "Comparing Soluble Ferric Pyrophosphate to Common Iron Salts and Chelates as Sources of Bioavailable Iron in a Caco-2 Cell Culture Model" Journal of Agricultural and Food Chemistry, US, vol. 57, No. 11, May 18, 2009 (May 18, 2009) (Year: 2009).*
Gupta et al. "Physicochemical characterization of ferric pyrophosphate citrate" Biometals, 31, 1091-1099 Oct. 15, 2018 (Oct. 15, 2018). (Year: 2018).*
Galbraith et al. "Media formulation optimization: current and future opportunities" Current Opinion in Chemical Engineering, 22:42-27 Oct. 4, 2018 (Oct. 4, 2018) (Year: 2018).*
Corning Minimum Essential Medium (MEM) Product formulation sheet (Year: 2013).*
Gupta et al., "Physicochemical characterization of ferric pyrophosphate citrate," *Biometals* 31(6): 1091-1099 (2018).
European Patent Office, International Search Report in International Application No. PCT/EP2020/072896 (Oct. 15, 2020).
European Patent Office, Written Opinion in International Application No. PCT/EP2020/072896 (Oct. 15, 2020).
International Bureau of WIPO, International Preliminary Report on Patentability in International Application No. PCT/EP2020/072896 (Feb. 17, 2022).
Keenan et al., "Replacement of transferrin by simple iron compounds for MDCK cells grown and subcultured in serum-free medium," *In Vitro Cell.Dev.Biol.-Animal* 32(8): 451-453 (1996).
Tian et al., "Dissolution behaviour of ferric pyrophosphate and its mixtures with soluble pyrophosphates: Potential strategy for increasing iron bioavailability," *Food Chemistry* 208: 97-102 (2016).
Zhu et al., "Comparing soluble ferric pyrophosphate to common iron salts and chelates as sources of bioavailable iron in a Caco-2 cell culture model," *J Agric Food Chem* 57(11): 5014-5019 (2009).
European Patent Office, Extended European Search Report in European Patent Application No. 19192089.1 (Jan. 31, 2020).

(Continued)

*Primary Examiner* — Allison M Fox
*Assistant Examiner* — Gina Pronzati
(74) *Attorney, Agent, or Firm* — Leydig, Voit & Mayer, Ltd.

(57) ABSTRACT

Disclosed is a cell culture medium for cultivating cells, containing an iron-citrate-diphosphate complex as an iron source. Also disclosed is a method for cultivating cells, one or more cells being replicated or maintained in the cell culture medium and to a method for expressing at least one recombinant protein in a cell culture, a nucleic acid being introduced into the cell replicated or maintained in the cell culture medium, wherein the nucleic acid causes the production of at least one recombinant protein. The cell culture medium is advantageous in that the iron source contained therein dissolves very efficiently and rapidly in an aqueous solution, can be efficiently imported into the interior of the cells, causes an increased cell viability and an increased product titer during the production of recombinant proteins, and is very inexpensive.

14 Claims, 5 Drawing Sheets

(56) References Cited

OTHER PUBLICATIONS

European Patent Office, First Notification under Article 94 (3) EPC in European Patent Application No. 19192089.1 (Aug. 5, 2020).
European Patent Office, Second Notification under Article 94 (3) EPC in European Patent Application No. 19192089.1 (Nov. 16, 2020).
European Patent Office, Third Notification under Article 94 (3) EPC in European Patent Application No. 19192089.1 (May 14, 2021).

\* cited by examiner

CELL CULTURE MEDIUM FOR CULTIVATING CELLS, METHOD FOR CULTIVATING CELLS, AND METHOD FOR EXPRESSING AT LEAST ONE RECOMBINANT PROTEIN IN A CELL CULTURE

CROSS-REFERENCE TO RELATED APPLICATIONS

This patent application is the U.S. national phase of International Application No. PCT/EP2020/072896, filed on Aug. 14, 2020, which claims the benefit of European Patent Application No. 19192089.1, filed Aug. 16, 2019, the disclosures of which are incorporated herein by reference in their entireties for all purposes.

A cell culture medium for cultivating cells comprising an iron citrate diphosphate complex as an iron source is provided. Furthermore, a method for cultivating cells is provided, in which one or more cell(s) is/are propagated or maintained in the cell culture medium according to the invention. In addition, a method for the expression of at least one recombinant protein in a cell culture is presented, in which a nucleic acid, which causes the production of at least one recombinant protein, has been introduced into the cell propagated or maintained in the cell culture medium according to the invention. The cell culture medium according to the invention has the advantage that its comprised iron source dissolves very well and quickly in an aqueous solution (for example, a cell culture medium, cell culture supplement or water), can be imported efficiently into the cell interior of the cells, causes an increased number of living cells and an increased product titer (also called product concentration) in the production of recombinant proteins, and is very cost-effective.

Cell culture media for cultivating biological cells may comprise an iron source, that is, a source of iron ions that can be efficiently imported by the biological cells. In fact, the presence of an iron source in the cell culture medium is essential for the cultivation of mammalian cells. The import of iron ions into biological cells can be achieved by adding, for example, the protein transferrin to a cell culture medium comprising an iron salt (for example, iron(III) nitrate, iron (II) sulfate and/or iron(III) chloride), because transferrin binds iron ions and makes them available in the cell culture medium in a way that is accessible (importable) to the biological cells.

Transferrin is usually obtained from blood plasma or produced recombinantly and is also commercially available in dry form. The disadvantage of the available transferrin is that it is expensive and therefore uneconomical for cell culture on an industrial scale. Furthermore, the available transferrin is already partially saturated with iron ions, so that the iron concentration in the cell culture medium cannot be adjusted in an exactly defined manner. There is therefore a need for transferrin-free cell culture media for the cultivation of biological cells. With such cell culture media, the iron ions must be offered to the biological cells effectively biologically accessible (that is, importable into the interior of the cells) in a different manner.

It is known in the prior art to make the iron in a different form effectively accessible to the cell culture media.

CA 2 756 247 C discloses that an iron salt or an iron complex can be used as an iron source in a serum-free medium. It is mentioned by way of example that the iron source can be selected from the group consisting of iron(III) phosphate, iron(III) pyrophosphate, iron(III) nitrate, iron(II) sulfate, iron(III) chloride, iron(II) lactate, iron(III) citrate, ammonium ferrous(II) citrate, iron dextran and EDTA iron sodium salt. However, many of the iron sources listed are not suitable for making the iron available to the biological cells in an easily accessible manner, so that it difficult to import the important iron ions into the cells. The result is that the cells grow more slowly and show low product titers when expressing recombinant proteins. Iron(II) citrate is the most effective of the iron sources mentioned, but has the disadvantage that it dissolves very slowly if it is present in a dry cell culture medium and said culture medium is prepared with water for cultivating the cells. The long dissolution period of iron(II) citrate represents a time disadvantage in the industrial production of cell culture media for the cultivation of cells, making the use of iron(II) citrate uneconomical.

WO 2016/156476 A1 discloses a transferrin-free cell culture medium which makes iron accessible to the biological cells via an iron choline citrate complex. The iron choline citrate complex is taught to be advantageous over commonly used iron sources such as iron(II) phosphate, iron(III) pyrophosphate and iron(III) citrate, because it contributes to significantly increased product titers in cell culture. However, the use of the iron-choline citrate complex in a cell culture medium has the disadvantage that the production costs of the cell culture medium are very high due to said iron complex and the cell culture medium therefore becomes uneconomical, especially when very large cell culture volumes are required.

It was therefore the object of the present invention to provide a cell culture medium that is free of transferrin (or completely serum-free) and comprises an iron source with which cell cultivation with high product titers can be carried out in a faster and less expensive (more economical) way. Furthermore, a corresponding method for cultivating cells and a corresponding method for expressing at least one recombinant protein in a cell culture should be provided.

The object is achieved by the cell culture medium having the features described herein, by the method for cultivating cells having the features described herein, by the method for expressing at least one recombinant protein in a cell culture having the features described herein and by the use of these features also described herein, as well as the advantageous developments thereof.

Figure 1A:
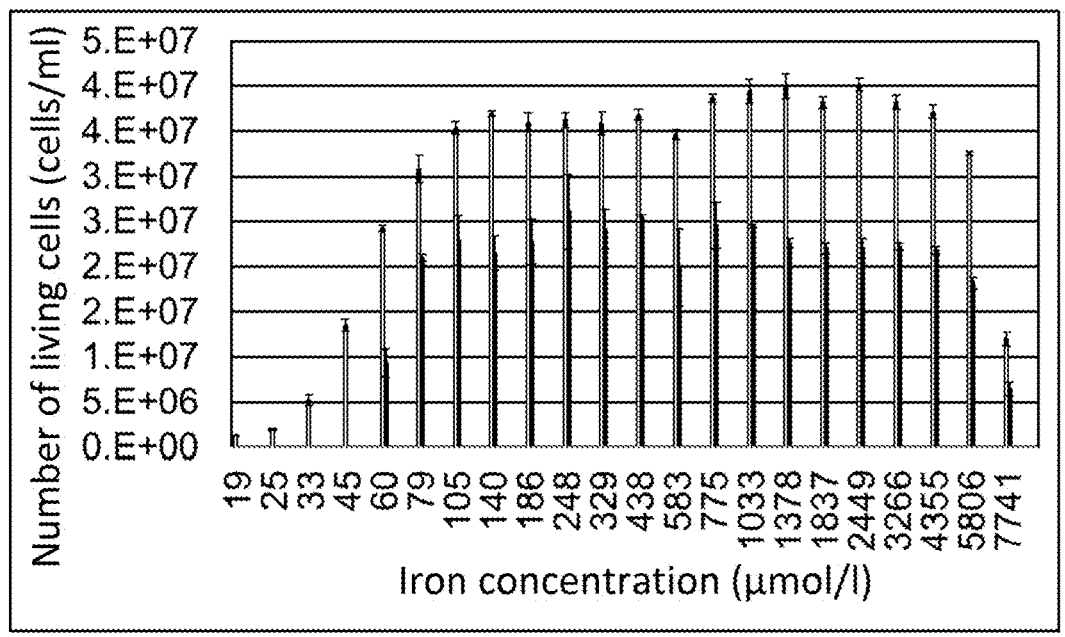
FIG. 1A shows the influence on cell growth by iron concentration (in µM) which was set via an iron citrate diphosphate sodium complex in a transferrin-free liquid culture medium.

According to the invention, a cell culture medium, which is characterized in that it comprises an iron citrate diphosphate complex, is provided.

The term "cell culture medium" is understood in particular to mean a nutrient substrate suitable for growing and maintaining biological cells (for example, microorganisms, plant, human and/or animal cells), optionally also viruses. This understanding of the term "cell culture medium" is based on the HS code 38210000 of the so-called "Harmonized Commodity Description and Coding Systems" (abbreviated: HS) defined by the "World Customs Organization" (abbreviated: WCO).

The cell culture medium can be based on Dulbecco's Modified Eagle's Medium/Ham's nutrient mixture F-12 (DMEM/F12).

The cell culture medium may comprise trace elements and salts, preferably of the elements calcium, iron, cobalt, copper, potassium, magnesium, manganese, molybdenum, sodium, nickel, phosphate, selenium, silicon, zinc and/or tin (most preferably all of these elements).

Furthermore, the cell culture medium can comprise essential and non-essential amino acids, preferably glycine, L-alanine, L-arginine, L-asparagine, L-aspartic acid, L-cysteine, L-cystine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine and/or L-valine (most preferably all of these).

The cell culture medium can comprise at least one component selected from the group consisting of biotin, choline, folinic acid, glucose, Hepes buffer, hypoxanthine, linoleic acid, lipoic acid, myoinositol, niacinamide, pantothenic acid, putrescine, pyridoxal, pyridoxine, riboflavin, thiamine, thymidine, pyruvate and vitamin B12 (preferably all of these components). Depending on the application, sodium bicarbonate and/or L-glutamine can be present in or added to the cell culture medium. For example, cell culture media in powder form usually do not comprise sodium bicarbonate. Sodium bicarbonate is often only added during the production of liquid cell culture media. Since L-glutamine breaks down spontaneously in aqueous solution, liquid cell culture media are often prepared without L-glutamine in order to increase their shelf life. In this case, L-glutamine is added as a stock solution, often just before use.

The cell culture medium according to the invention has the advantage that it does not require transferrin from blood serum or recombinant transferrin as an iron supplier and, in relation to comparable cell culture media in the prior art, enables cell cultivation with high product titers in a faster and less expensive (more economical) manner, because the iron citrate diphosphate complex present in the cell culture medium dissolves very quickly and well in aqueous solutions (for example, media, supplements or water) and is less expensive than the known use of an iron-choline citrate complex in cell culture medium.

In a preferred embodiment, the cell culture medium is present in undissolved form, preferably in the form of a powder or granulate. The advantage here is that the cell culture medium has a long shelf life and transport costs are lower than in the case of a cell culture medium in dissolved form. The cell culture medium preferably comprises the iron citrate diphosphate complex in an amount of 0.16% by weight to 12% by weight, preferably 0.22% by weight to 6% by weight, particularly preferably 0.3% by weight to 2% by weight, very particularly preferably 0.4% by weight to 1% by weight, in particular 0.5% by weight to 0.7% by weight.

The cell culture medium can be present in dissolved form, preferably in the form of an aqueous solution. The advantage here is that the time for adding water and dissolving the cell culture medium in water is eliminated, so that the cultivation of biological cells can be started immediately. The dissolved cell culture medium preferably comprises the iron citrate diphosphate complex in an amount such that the iron concentration of the cell culture medium set via the (undissociated) iron citrate diphosphate complex is in the range from 80 µM to 5800 µM, preferably 100 µM to 3000 µM, particularly preferably 150 µM to 1000 µM, very particularly preferably 200 µM to 5000 µM, in particular 250 µM to 350 µM.

In particular, the iron citrate diphosphate complex is present in the dissolved cell culture medium in an undissociated form (see, for example, p. 1097, right column, first paragraph in Gupta et al., Physicochemical characterization of ferric pyrophosphate citrate, Biometals, 2018, vol. 31, pp. 1091-1099). Consequently, the iron concentration set via the iron citrate diphosphate complex means an iron concentration resulting from the undissociated iron citrate diphosphate complex. In other words, the iron concentration set via the iron citrate diphosphate complex in the cell culture medium refers to a concentration of iron atoms that are present complexed in the iron citrate diphosphate complex, that is, not to a concentration of iron atoms that are present in the cell culture medium in free form (for example, free $Fe'$ ions and/or $Fe'$ ions). If the iron citrate diphosphate complex has 4 iron atoms (see, for example, FIG. 5b in Gupta et al.), the dissolved cell culture medium thus comprises the iron citrate diphosphate complex preferably in an amount of 20 µM to 1450 µM, preferably 25 µM to 750 µM, particularly preferably 37.5 µM to 250 µM, very particularly preferably 50 µM to 1250 µM, in particular 62.5 µM to 87.5 µM in order to set the iron concentration of the cell culture medium to the ranges mentioned above.

The iron citrate diphosphate complex can be selected from the group consisting of iron citrate diphosphate sodium complex, iron citrate diphosphate potassium complex, iron citrate diphosphate ammonium complex, and mixtures thereof. The iron citrate diphosphate complex is preferably an iron citrate diphosphate sodium complex, particularly preferably an iron citrate diphosphate sodium complex with CAS No. 85338-24-5 and/or EC No. 286-697-4. The advantage of the iron citrate diphosphate sodium complex compared to the other complexes is that sodium ions, in contrast to other cations such as ammonium, are even tolerated in higher concentrations in the cell culture medium by many biological cells.

In a preferred embodiment, the cell culture medium is free of at least one serum component, preferably free of transferrin and/or lactotransferrin.

The cell culture medium may comprise a serum substitute, preferably an Ultroser G serum substitute in the composition available in August 2018. In this case, the cell culture medium is in particular free of transferrin and/or lactotransferrin.

Furthermore, the cell culture medium can comprise growth factors. In this case, the cell culture medium is in particular free of transferrin and/or lactotransferrin.

In a preferred embodiment, the cell culture medium is free of animal or human components.

The cell culture medium can be protein-free.

Furthermore, the cell culture medium can be hydrolyzate-free.

In addition, the cell culture medium can be chemically-defined.

The cell culture medium can be characterized in that it comprises at least one, preferably a plurality of, amino acid(s), the at least one, preferably plurality of, amino acid(s) being preferably selected from the group consisting of alanine, arginine, asparagine, aspartic acid, cysteine, cystine, glutamine, glutamic acid, glycine, histidine, isoleucine, leucine, lysine, methionine, phenylalanine, proline, serine, threonine, tryptophan, tyrosine, valine and combinations and/or salts thereof, the cell culture medium comprising in particular all of said amino acids.

Furthermore, the cell culture medium can be characterized in that it comprises at least one, preferably a plurality of, lipid precursor(s), the at least one, preferably plurality of, lipid precursor(s) being preferably selected from the group consisting of choline chloride, ethanolamine, glycerol, inositol, linolenic acid, fatty acid, phospholipid, cholesterol-related compounds, and combinations and salts thereof.

In addition, the cell culture medium can be characterized in that it comprises at least one, preferably a plurality of, carboxylic acid(s) having at least six carbon atoms, the at least one, preferably plurality of, carboxylic acid(s) being preferably selected from the group consisting of linoleic acid, linolenic acid, thioctic acid, oleic acid, palmitic acid, stearic acid, arachidic acid, arachidonic acid, lauric acid, behenic acid, decanoic acid, dodecanoic acid, hexanoic acid, lignoceric acid, myristic acid, octanoic acid and combinations and salts thereof, the cell culture medium comprising in particular all of said fatty acids and/or salts thereof.

It is possible that the cell culture medium is characterized in that it comprises at least one, preferably a plurality of, carboxylic acid(s) having fewer than six carbon atoms, the at least carboxylic acid preferably being butyric acid or a salt of butyric acid.

In an advantageous embodiment, the cell culture medium is characterized in that it comprises at least one, preferably a plurality of, nucleoside(s), the at least one, preferably plurality of, nucleoside(s) being selected from the group consisting of adenosine, guanosine, cytidine, uridine, thymidine, hypoxanthine and combinations and salts thereof, in particular the cell culture medium comprising all of said nucleosides and/or salts thereof.

Furthermore, the cell culture medium can be characterized in that it comprises at least one, preferably a plurality of, carbohydrate(s), the at least one, preferably plurality of, carbohydrate(s) being preferably selected from the group consisting of glucose, galactose, glucosamine, fructose, mannose, ribose, sucrose, and combinations thereof.

The cell culture medium can be characterized in that it comprises at least one, optionally a plurality of, buffer substance(s), the at least one, optionally plurality of, buffer substance(s) being preferably selected from the group consisting of ACES, HEPES, MES, MOPS, $NaHCO_3$, PIPES, phosphate buffer, TRIS and combinations and/or salts thereof.

Furthermore, the cell culture medium can be characterized in that it comprises at least one, preferably a plurality of, trace element(s), optionally further comprises a chelating agent, preferably EDTA, the at least one, preferably plurality of, trace element(s) being preferably selected from the group consisting of calcium, cobalt, copper, potassium, magnesium, manganese, molybdenum, sodium, nickel, phosphate, selenium, vanadium, zinc, tin and combinations thereof, the trace element being able to optionally be present in salt form and the cell culture medium in particular comprising all of said trace elements.

In addition, the cell culture medium can be characterized in that it comprises at least one, preferably a plurality of, vitamin(s), the at least one, preferably plurality of, vitamin(s) being preferably selected from the group consisting of biotin, choline, folinic acid, myoinositol, niacinamide (B3), pantothenic acid, pyridoxal, pyridoxine, riboflavin, thiamine, vitamin B12 and comprising combinations and/or salts thereof.

In a preferred embodiment, the cell culture medium, particularly preferably in undissolved form, comprises no iron salt.

Furthermore, the cell culture medium can be characterized in that it, particularly preferably in undissolved form, comprises no iron citrate, preferably no citrate salt and/or no citric acid.

In addition, the cell culture medium can be characterized in that it, particularly preferably in undissolved form, comprises no iron diphosphate, preferably no diphosphate salt and/or no diphosphoric acid.

The cell culture medium can be characterized in that it comprises a cell culture medium selected from the group consisting of DMEM, DMEM/F12 Media, Ham's F-10 Media, Ham's F-12 Media, Medium 199, MEM, RPMI 1640 Medium, ISF-1, Octomed, Ames' Medium, BGJb Medium (optionally in the Fitton-Jackson Modification), Click's Medium, CMRL-1066 Medium, Fischer's Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E and combinations thereof, optionally also modifications thereof, the respective cell culture medium being meant in the composition available in August 2018.

In a preferred embodiment, the cell culture medium is characterized in that it comprises a cell culture medium selected from the group consisting of DMEM, DMEM/F12 Media, Ham's F-10 Media, Ham's F-12 Media, Medium 199, MEM, RPMI 1640 Medium and combinations thereof, optionally also modifications thereof, the respective cell culture medium being meant in the composition available in August 2018.

According to the invention, a method for cultivating cells is also provided, comprising the following steps:
  a) providing a cell culture medium as described herein in an aqueous solution; and
  b) propagating or maintaining at least one cell in the aqueous solution of the cell culture medium.

The cell in this case can be a cell of a primary cell line or a continuous cell line and preferably be selected from the group consisting of mammalian cell, bird cell and insect cell, the cell particularly preferably being a mammalian cell, particularly preferably a mammalian cell selected from the group consisting of CHO, NS0, SP2/0, hybridoma, HEK293, PERC-6, BHK-21 and Vero-76, very particularly preferably a CHO cell, in particular a CHO cell selected from the group consisting of CHO-DG44, CHO-DUKX, CHO-S and CHO-K1.

In addition, according to the invention, a method for the expression of at least one recombinant protein in a cell culture is provided, in which case the method according to the invention for cultivating cells further comprises introducing a nucleic acid into the at least one cell, the nucleic acid causing a constitutive or induced production of at least one recombinant protein, preferably additionally causing secretion of the protein produced into the aqueous solution of the cell culture medium, the recombinant protein being particularly preferably selected from the group consisting of therapeutic protein, antibody, fusion protein, enzyme, vaccine, biosimilar and combinations thereof.

According to the invention, the use of an iron citrate diphosphate complex (preferably an iron citrate diphosphate sodium complex, in particular with CAS No. 85338-24-5 and/or EC No. 286-697-4) in a cell culture medium is proposed, preferably as an ingredient in a cell culture medium for the cultivation of at least one cell in the cell culture medium and/or as an additive in a cell culture medium during a cultivation of at least one cell in the cell culture medium. The iron citrate diphosphate complex can be used such that the cell culture medium has at least one of the properties mentioned above. For example, the iron citrate diphosphate complex can be used in one of the concentrations mentioned above in the cell culture medium. Furthermore, the iron citrate diphosphate complex can be used as an ingredient and/or additive in a cell culture medium for the cultivation of at least one of the abovementioned cells.

DETAILED DESCRIPTION OF THE INVENTION

The subject according to the invention is to be explained in more detail on the basis of the following examples and figures, without wishing to restrict it to the specific embodiments presented here.

Figure 1B:
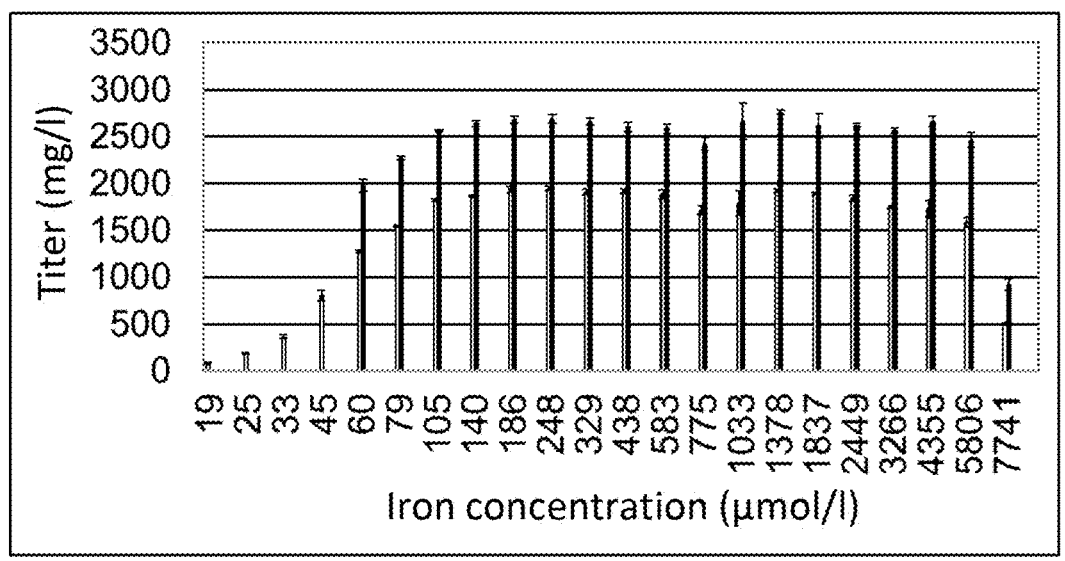
FIG. 1B shows the influence on protein production by cells which have been genetically modified to produce a specific protein.

FIG. 1A-1B show the influence of an iron concentration (in μM) which was set via an iron citrate diphosphate sodium complex in a transferrin-free liquid culture medium, on cell growth and protein production of cells which have been genetically modified to produce a specific protein. The x-axis represents the iron concentration set in the liquid medium. The number of living cells determined (in cells per mL) after 10 days (white bars) and after 13 days (black bars) from the start of the cell culture experiment (fed batch) are depicted on the y-axis in FIG. 1A. The product concentration determined (titer in mg/L) after 10 days (white bars) and after 13 days (right black bars) from the start of the cell culture experiment (fed batch) is depicted on the y-axis in FIG. 1B. It can be seen that the optimum iron concentration set via the iron citrate diphosphate sodium complex is in the range of approx. 80 μM to 5800 μM.

Figure 2A:
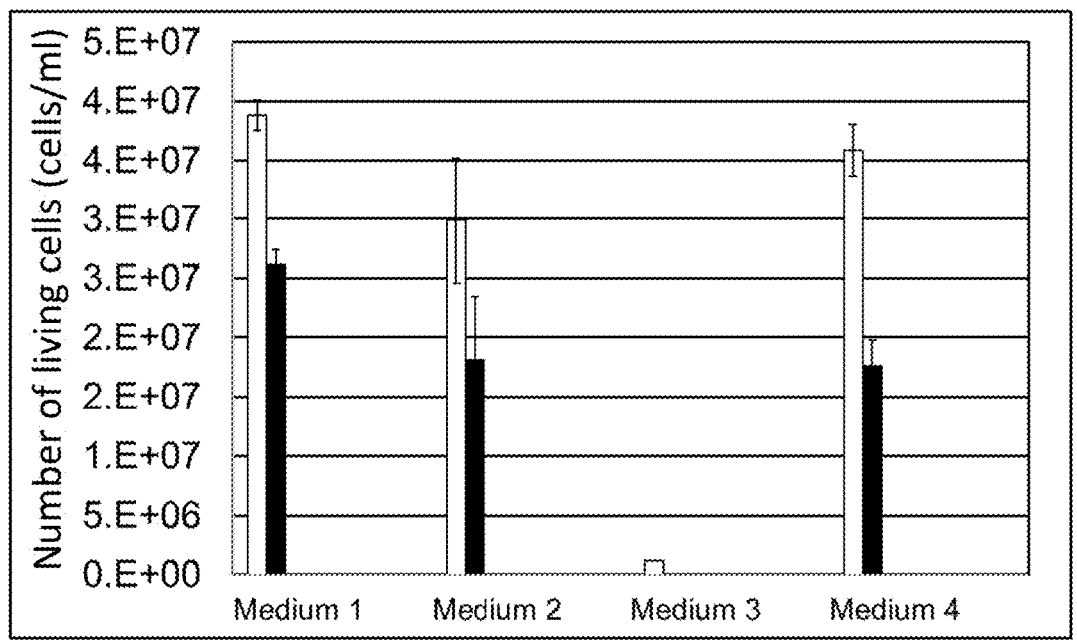
FIG. 2A show the number of living cells as a function of an iron concentration of 300 µM, which was set via an iron citrate diphosphate sodium complex in a transferrin-free liquid culture medium.
Figure 2B:
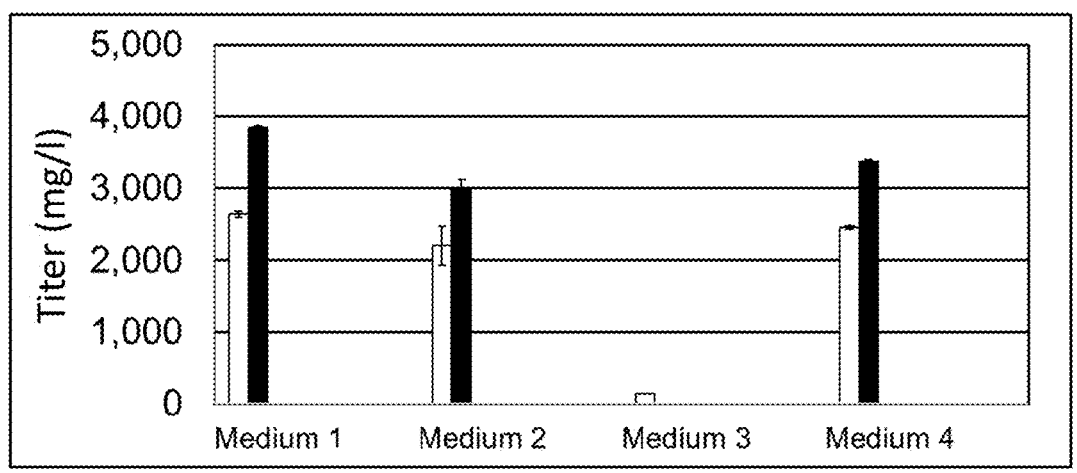
FIG. 2B shows the effect on protein production of cells that have been genetically modified to produce a specific protein, in comparison to an iron concentration of 300 µM which was set via another iron source in the same medium.

FIG. 2A-2B show the effect of an iron concentration of 300 μM, which was set via an iron citrate diphosphate sodium complex in a transferrin-free liquid culture medium, on cell growth and protein production of cells that have been genetically modified to produce a specific protein, in comparison to an iron concentration of 300 μM which was set via another iron source in the same medium. In other words, the four Media 1, 2, 3 and 4 depicted on the x-axis are identical in their composition except for the iron source which was used to set the iron concentration of 300 μM. In Medium 1, the iron source is an iron citrate diphosphate sodium complex; in Medium 2, the iron source is iron (II) sulfate heptahydrate; in Medium 3, the iron source is iron (III) nitrate nonahydrate; in Medium 4, the iron source is iron (III) citrate. The number of living cells determined (in cells per mL) after 10 days (white bars) and after 13 days (black bars) from the start of the cell culture experiment (fed batch) are depicted on the y-axis in FIG. 2A. The product concentration determined (titer in mg/L) after 10 days (white bars) and after 13 days (black bars) from the start of the cell culture experiment (fed batch) is depicted on the y-axis in FIG. 1B. It can be seen that the iron source present in Medium 1 (iron citrate diphosphate sodium complex), with respect to the iron sources present in Media 2 to 4, had a beneficial effect on the number of the living cells and on the product concentration, that is, on the amount of product produced, at 10 days and at 13 days from the start of the experiment.

Figure 3:
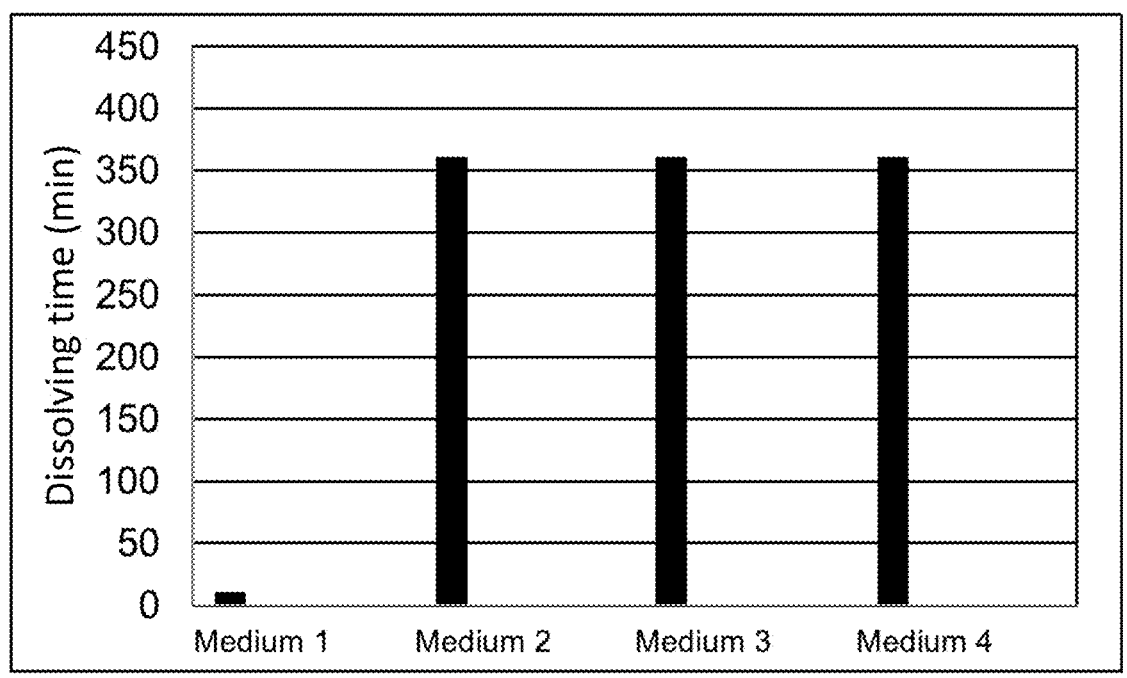
FIG. 3 shows the time it takes for a powdered transferrin-free culture medium, to which an iron citrate-diphosphate-sodium complex has been added as an iron source, to be completely dissolved in water in comparison to media which have the same composition and differ only in the iron source.

FIG. 3 shows the time it takes for a powdered transferrin-free culture medium, to which an iron citrate-diphosphate-sodium complex has been added as an iron source, to be completely dissolved in water in comparison to media which have the same composition and differ only in the iron source. In other words, the four Media 1, 2, 3 and 4 depicted on the x-axis are identical in their composition except for the iron source used to set an iron concentration of 300 μM. In Medium 1, the iron source is an iron citrate diphosphate sodium complex; in Medium 2, the iron source is iron (II) sulfate heptahydrate; in Medium 3, the iron source is iron (III) nitrate nonahydrate; in Medium 4, the iron source is iron (III) citrate. The y-axis shows the time (in minutes) until the initially dry, powdery medium has completely dissolved in water, wherein more than 360 minutes were required to completely dissolve the initially dry, powdery Media 2, 3 and 4. It can be seen that the dry, powdery Medium 1 having the iron citrate diphosphate sodium complex as the iron source dissolves much more quickly in water than Media 2, 3 and 4 which have a different iron source.

Figure 4A:
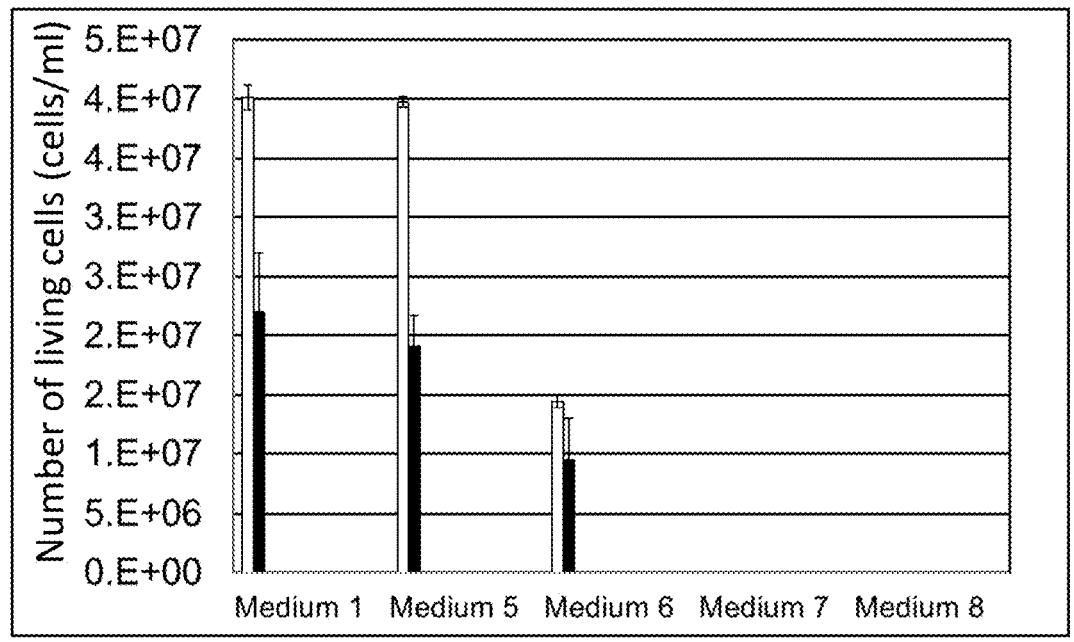
FIG. 4A shows the result of a further experiment on the effect of an iron concentration of 300 µM, which was set via an iron citrate diphosphate sodium complex in a transferrin-free liquid culture medium, on cell growth.
Figure 4B:
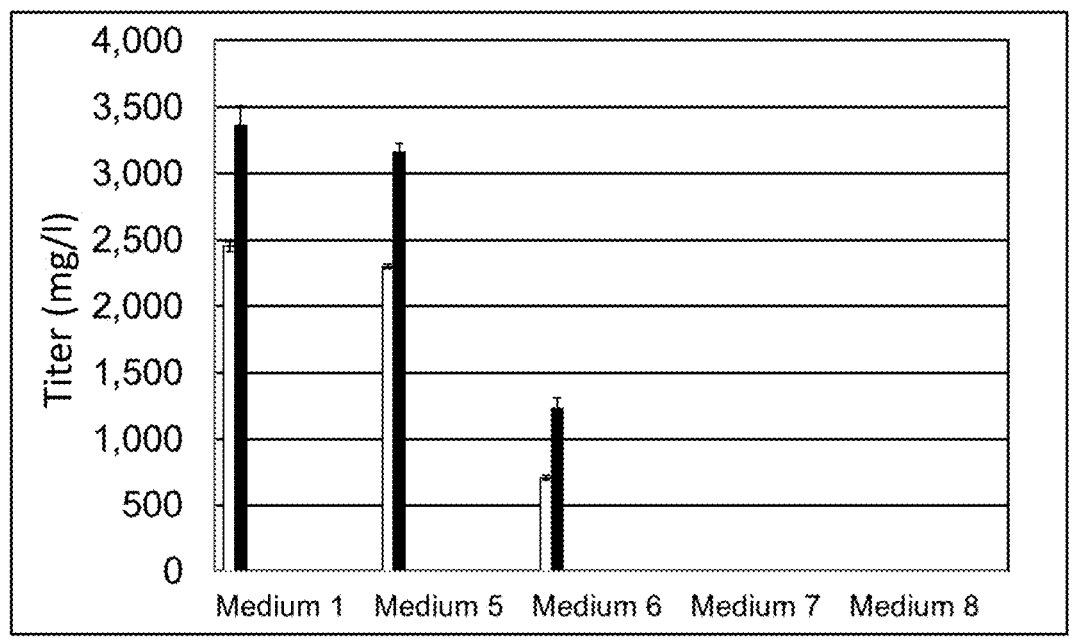
FIG. 4B shows the effect on protein production of cells that have been genetically modified to produce a specific protein, compared to an iron concentration of 300 µM set via another iron source in the same medium.

FIG. 4A-4B show the result of a further experiment on the effect of an iron concentration of 300 μM, which was set via an iron citrate diphosphate sodium complex in a transferrin-free liquid culture medium, on cell growth and protein production of cells that have been genetically modified to produce a specific protein, compared to an iron concentration of 300 μM set via another iron source in the same medium. In other words, the five Media 1, 5, 6, 7 and 8 depicted on the x-axis are identical in their composition except for the iron source used to adjust the iron concentration of 300 μM. The number of living cells determined (in cells per ml) after 10 days (white bars) and after 13 days (black bars) from the start of the cell culture experiment (fed batch) are depicted on the y-axis in FIG. 4A. The product concentration determined (titer in mg/l) after 10 days (white bars) and after 13 days (black bars) from the start of the cell culture experiment (fed batch) is depicted on the y-axis in FIG. 1B. It can be seen that the iron source present in Medium 1 (iron citrate diphosphate sodium complex), with respect to the iron sources present in Media 6 to 8, had a beneficial effect on the number of living cells at 10 days and at 13 days from the start of the experiment. It can further be seen that the iron source present in Medium 1 (iron citrate diphosphate sodium complex), with respect to iron sources present in Media 5 to 8, has a beneficial effect on product concentration, that is, the amount of product produced, at 10 days and 13 days from the start of the experiment. The experiment proves that the iron citrate diphosphate sodium complex does not form in the liquid media from its individual components, because if it did, the values obtained in Media 5 to 8 would have to be identical to the values obtained for Medium 1. However, this was not the case. It is also demonstrated that the iron citrate diphosphate sodium complex (in Medium 1) is beneficial to the amount of obtained, manufactured product compared to a mixture of iron (III) citrate and sodium tetrabasic pyrophosphate. (compare Media 1 and 5 in FIG. 4B).

Figure 5:
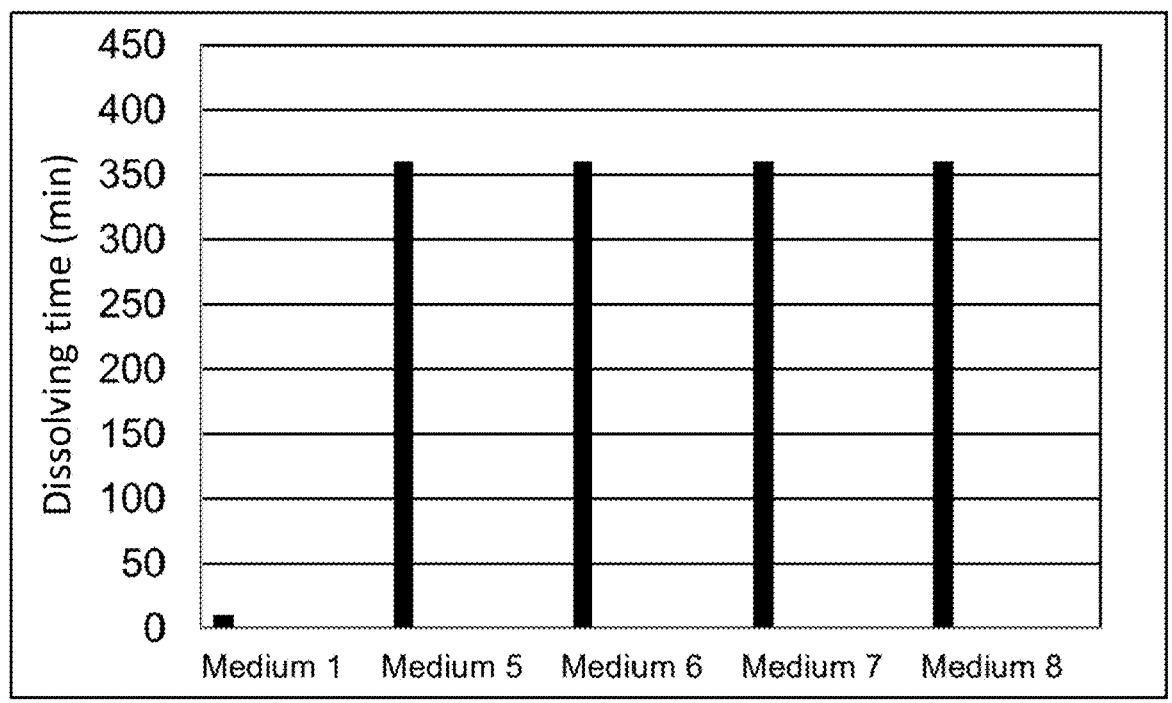
FIG. 5 shows the time it takes for a powdered transferrin-free culture medium to which an iron citrate-diphosphate-sodium complex has been added as an iron source to be completely dissolved in water in comparison to media which have the same composition and differ only in that the components of the iron citrate diphosphate complex are present in the form of individual components.

FIG. 5 shows the time it takes for a powdered transferrin-free culture medium to which an iron citrate-diphosphate-sodium complex has been added as an iron source to be completely dissolved in water in comparison to media which have the same composition and differ only in that the components of the iron citrate diphosphate complex are present in the form of individual components. In other words, the five Media 1, 5, 6, 7 and 8 depicted on the x-axis are comparable in their composition except for the source of iron, citrate and pyrophosphate. The time (in minutes) required for the originally dry, powdery medium to completely dissolve in water is given on the y-axis. It can be seen that the dry, powdery Medium 1 having the iron citrate diphosphate sodium complex, compared to the Media 5, 6, 7 and 8, which have the individual components of the iron citrate diphosphate complex (that is, salts for providing iron ions, citrate ions, pyrophosphate ions and sodium ions), dissolved in water significantly faster, wherein more than 360 minutes were required to achieve complete dissolution of the originally dry, powdered Media 5, 6 and 7, and Medium 8 did not dissolve completely.

EXAMPLE 1—BIOLOGICAL CELLS THAT CAN BE CULTIVATED WITH THE CELL CULTURE MEDIUM ACCORDING TO THE INVENTION

| Cell line | Example of this cell line |
| --- | --- |
| NS0 | ECACC No. 85110503 |
| Sp2/0-Ag14 | ATCC CRL-1581 |
| BHK21 | ATCC CCL-10 |
| BHK TK- | ECACC No. 85011423 |
| HaK | ATCC CCL-15 |
| 2254-62.2 (BHK-21 derivative) | ATCC CRL-8544 |
| CHO | ECACC No. 8505302 |
| CHO wild type | ECACC 00102307 |
| CHO-K1 | ATCC CCL-61 |
| CHO-DUKX (=CHO duk-, CHO/dhfr-) | ATCC CRL-9096 |
| CHO-DUKX B11 | ATCC CRL-9010 |
| CHO-DG44 | Urlaub et al., 1983 |
| CHO Pro-5 | ATCC CRL-1781 |
| CHO-S | Freedom ™ CHO-S ™ Kit, Thermo Fisher Scientific Cat no. R800-07 |
| V7 | ATCC CCC-93 |
| B14AF28-G3 | ATCC CCL-14 |
| PER.C6 | (Fallaux, F. J. et al, 1998) |
| HEK 293 | ATCC CRL-1573 |
| COS-7 | ATCC CRL-1651 |
| U26 | ATCC TIB-196 |
| HuNS1 | ATCC CRL-8644 |
| CHL | ECACC No. 87111906 |
| PER-C6 | |
| human liver cells | Hep G2, HB 8065 |
| human lung cells | W138, ATCC CCL 75 |
| human cervical carcinoma cells | (HeLa, ATCC CCL 2) |
| monkey kidney cells | COS- 7, ATCC CRL 1651 |
| canine kidney cells | MDCK |
| monkey kidney cells | CV1, ATCC CCL 70 |
| African green monkey kidney cells | VERO-76, ATCC CRL-1587 |
| baby hamster kidney cells | BHK-21, ATCC CCL 10 |
| Chinese hamster ovary cells | CHO-DG44 |
| CHO-DUKX | |
| CHO-K1 | ATCC CCL 61 |
| lymphocytic cells | Jurkat T-cell line) |
| buffalo rat liver cells | BRL 3A, ATCC CRL 1442 |
| mouse mammary tumor cells | MMT 060562, ATCC CCL 51 |
| SP2/0 cells | |
| myeloma cells | NS0 |
| hybridoma cells | |
| trioma cells. | |

EXAMPLE 2—DETERMINATION OF THE OPTIMAL CONCENTRATION OF THE IRON CITRATE DIPHOSPHATE COMPLEX IN THE CELL CULTURE MEDIUM

In order to determine the optimal concentration range for the iron citrate diphosphate complex in the cell culture medium, an iron citrate diphosphate sodium complex was tested in different concentrations in a transferrin-free cell culture medium.

The cell culture medium used was based on Dulbecco's Modified Eagle's Medium/Ham's nutrient Mixture F-12 (DMEM/F12-Medium). Said medium comprised trace elements and salts of the elements calcium, iron, cobalt, copper, potassium, magnesium, manganese, molybdenum, sodium, nickel, phosphate, selenium, silicon, zinc and tin. The iron concentration in the used cell culture medium, without the addition of the iron citrate diphosphate complex, was below 0.8 M. Furthermore, the cell culture medium used comprised glycine, L-alanine, L-arginine, L-asparagine, L-aspartic acid, L-cysteine, L-cystine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine and L-valine. In addition, the cell culture medium used comprised biotin, choline, folinic acid, glucose, Hepes buffer, hypoxanthine, linoleic acid, lipoic acid, myoinositol, niacinamide, pantothenic acid, putrescine, pyridoxal, pyridoxine, riboflavin, thiamine, thymidine, pyruvate and vitamin B12.

The cell growth of cells that were genetically modified to produce a specific protein was investigated as a function of the iron concentration, which was set via the iron citrate diphosphate sodium complex in the liquid cell culture medium which was dissolved in water and was based on the above-mentioned DMEM/F12 medium. In addition, the production of the desired protein product was investigated as a function of the iron concentration in the liquid medium which was set via the iron citrate diphosphate sodium complex.

The following table gives the respective weight of the iron citrate diphosphate complex in mg per liter of liquid medium (concentration of the iron citrate diphosphate complex in mg/l) that was used to set the respective desired iron concentration in the liquid medium.

TABLE

| Concentration of iron citrate diphosphate complex in mg/l | Adjusted concentration of iron ions in μM |
| --- | --- |
| 9.5 | 19.4 |
| 12.2 | 24.8 |
| 16.3 | 33.3 |
| 22.0 | 45.0 |

TABLE-continued

| Concentration of iron citrate diphosphate complex in mg/l | Adjusted concentration of iron ions in µM |
|---|---|
| 29.3 | 59.7 |
| 38.8 | 79.1 |
| 51.7 | 105.4 |
| 68.8 | 140.3 |
| 91.2 | 186.0 |
| 121.6 | 248.0 |
| 161.5 | 329.4 |
| 214.7 | 437.9 |
| 285.8 | 582.8 |
| 380.0 | 775.0 |
| 506.5 | 1033.1 |
| 675.6 | 1378.0 |
| 900.6 | 1836.8 |
| 1200.8 | 2449.0 |
| 1601.3 | 3265.9 |
| 2135.2 | 4354.7 |
| 2846.6 | 5805.5 |
| 3795.8 | 7741.5 |

The results of cell growth and protein production as a function of the iron concentration set via the iron citrate diphosphate sodium complex are depicted in FIGS. 1A and 1B. It was found that a final iron concentration in the range from approx. 80 µM to 5800 µM in the liquid medium represents an optimum for cell growth and protein production. Since the iron concentration in the cell culture medium used was below 0.8 µM without the addition of the iron citrate diphosphate complex, this final iron concentration in the range from approx. 80 µm to 5800 µm was achieved by using a practically corresponding molar amount of the iron citrate diphosphate complex (that is, approx. 80 µm to 5800 µm iron citrate diphosphate sodium complex).

EXAMPLE 3—INFLUENCE OF IRON CITRATE DIPHOSPHATE SODIUM COMPLEX ON CELL GROWTH AND PROTEIN PRODUCTION COMPARED TO OTHER IRON SOURCES

A total of four different media were tested which, apart from the iron source used, corresponded to the transferrin-free culture medium listed in Example 2 and thus had an identical composition apart from the iron source used. The iron source used was added to all media in an amount such that a final iron concentration of 300 µM was reached in the liquid medium.

The iron source used was:
Medium 1: iron citrate diphosphate sodium complex (300 µM iron concentration);
Medium 2: iron(II) sulfate heptahydrate (300 µM iron concentration);
Medium 3: iron(III) citrate nonahydrate (300 µM iron concentration);
Medium 4: iron(III) citrate (300 µM iron concentration).

The influence on cell growth and protein production of the cultivated cells genetically modified to produce a specific protein was investigated after 10 days and after 13 days from the start of the cell culture experiment (fed batch). The result is depicted in FIGS. 2A and 2B. It was shown that the iron source present in Medium 1 (iron citrate diphosphate sodium complex), with respect to the iron sources present in Media 2 to 4, had a beneficial effect on the number of the living cells and on the product concentration, that is, on the amount of product produced, at 10 days and at 13 days from the start of the experiment.

EXAMPLE 4—SOLUBILITY OF A DRY MEDIUM HAVING THE IRON SOURCE IRON CITRATE DIPHOSPHATE SODIUM COMPLEX IN WATER COMPARED TO DRY MEDIUM HAVING OTHER IRON SOURCES

Water was added to the media from Example 3 in dry, powdered form, and the time was measured for each of the dry, powdered media to have completely dissolved. The results are depicted in FIG. 3. It can be seen that the dry, powdery Medium 1 having the iron citrate diphosphate sodium complex as the iron source dissolves significantly faster in water than the Media 2, 3 and 4, which have a different iron source, wherein more than 360 minutes were needed to achieve complete dissolution of the initially dry, powdered Media 2, 3 and 4.

EXAMPLE 5—INFLUENCE OF IRON CITRATE DIPHOSPHATE SODIUM COMPLEX COMPARED TO OTHER IRON SOURCES, WHICH ADDITIONALLY HAVE INDIVIDUAL COMPONENTS OF THE IRON CITRATE DIPHOSPHATE SODIUM COMPLEX ON THE GROWTH AND PROTEIN PRODUCTION OF THE CELLS

A total of five different media were tested which, apart from the iron source used, corresponded to the transferrin-free culture medium listed in Example 2 and, apart from the iron source used and certain individual components of the iron citrate-diphosphate-sodium complex, had an identical composition. The iron source used was added to all media in an amount such that a final iron concentration of 300 µM was reached in the liquid medium. The additional individual components of the iron citrate-diphosphate-sodium complex from Medium 1, which should allow formation of the complex in the dissolved medium, were added to the comparison Media 5, 6, 7 and 8 in equimolar amounts as far as possible. An iron to citrate to pyrophosphate ratio of 4 to 3 to 3 was used to calculate the equimolar amounts of pyrophosphate and citrate, which was determined by X-ray absorption spectroscopy according to Gupta et al. (Physicochemical characterization of ferric pyrophosphate citrate, Biometals, 2018, vol. 31, pp. 1091-1099.) In other words, the amount of pyrophosphate and citrate in Media 5 to 8 was maintained comparable to the concentration of pyrophosphate and citrate in Medium 1 provided by the iron citrate diphosphate sodium complex. The aim was to investigate whether the individual components of the iron citrate-diphosphate-sodium complex have a comparable effect to the complex or whether the complex could form spontaneously from the individual components in aqueous solution.

The five media tested comprised as an iron source, pyrophosphate source and citrate source:
Medium 1: iron citrate diphosphate sodium complex (300 µM iron concentration);
Medium 5: iron(III) citrate (300 µM iron concentration) tetrabasic sodium pyrophosphate (225 µM pyrophosphate concentration);
Medium 6: iron(II) sulfate heptahydrate (300 µM iron concentration)
tetrabasic sodium pyrophosphate (225 µM pyrophosphate concentration)
tribasic sodium citrate dihydrate (225 µM citrate concentration)

Medium 7: iron(III) nitrate nonahydrate (300 µM iron concentration)
tetrabasic sodium pyrophosphate (225 µM pyrophosphate concentration)
tribasic sodium citrate dihydrate (225 µM citrate concentration)

Medium 8: iron(III) pyrophosphate (300 µM iron concentration)
tribasic sodium citrate dihydrate (225 µM citrate concentration)

The influence on cell growth and protein production of the cultivated cells genetically modified to produce a specific protein was investigated after 10 days and after 13 days from the start of the cell culture experiment (fed batch). The result is depicted in FIGS. 4A and 4B. It was revealed that the iron source present in Medium 1 (iron citrate diphosphate sodium complex), with respect to the iron sources present in Media 6 to 8, had a beneficial effect on the number of living cells at 10 days and at 13 days from the start of the experiment of living cells. It can further be seen that the iron source present in Medium 1 (iron citrate diphosphate sodium complex), with respect to iron sources present in Media 5 to 8, has a beneficial effect on product concentration, that is, the amount of product produced, at 10 days and 13 days from the start of the experiment.

The experiment proves that the iron citrate diphosphate sodium complex does not form in the liquid media from its individual components, otherwise the results for Media 5 to 8 would have to be identical to the result for Medium 1. However, this was not the case.

The data further show that the iron citrate diphosphate sodium complex (Medium 1) is beneficial with respect to a mixture of iron(III) citrate and tetrabasic sodium pyrophosphate (Medium 5) in terms of the obtained amount of product produced. (compare Media 1 and 5 in FIG. 4B). Since Medium 5 comprises pyrophosphate in free, anionic form and not in complexed form (in the iron citrate diphosphate sodium complex), this could mean that pyrophosphate bound to the cells in the iron citrate diphosphate sodium complex is more accessible, that is, can be taken up more easily than free, anionic pyrophosphate and thus the intracellular pyrophosphate concentration that can be achieved via the iron citrate-diphosphate-sodium complex is higher than is possible with free pyrophosphate in the medium.

Medium 5 to Medium 8 were prepared to show that iron complex does not spontaneously form itself and that there is a performance difference.

EXAMPLE 6—SOLUBILITY OF A DRY MEDIUM HAVING THE IRON CITRATE DIPHOSPHATE SODIUM COMPLEX IN WATER COMPARED TO DRY MEDIA HAVING OTHER INDIVIDUAL COMPONENTS OF THE COMPLEX (THAT IS, IRON, CITRATE AND PYROPHOSPHATE AS INDIVIDUAL COMPONENTS)

Water was added to the media from Example 5 in dry, powdered form, and the time was measured for each of the dry, powdered media to have completely dissolved. The results are depicted in FIG. 5. It is clear that the dry, powdery Medium 1 having the iron citrate diphosphate sodium complex, compared to the Media 5, 6, 7 and 8, which have the individual components of the iron citrate diphosphate complex (that is, salts for providing iron ions, citrate ions, pyrophosphate ions and sodium ions), dissolved in water significantly faster, wherein more than 360 minutes were required to achieve complete dissolution of the originally dry, powdered Media 5, 6 and 7, and Medium 8 did not dissolve completely.

The invention claimed is:

1. A cell culture medium comprising an iron citrate diphosphate complex,
wherein the iron citrate diphosphate complex is present in
i) an undissolved form, wherein the cell culture medium comprises the iron citrate diphosphate complex in an amount of 0.16% by weight to 12% by weight; or
ii) a dissolved form, wherein the cell culture medium comprises the dissolved iron citrate diphosphate complex in an amount that the iron concentration of the cell culture medium set via the iron citrate diphosphate complex is in a range from 80 µM to 5800 µM;
wherein the iron citrate diphosphate complex is an iron citrate diphosphate sodium complex.

2. The cell culture medium of claim 1, wherein the iron citrate diphosphate complex is present in undissolved form and the cell culture medium is a powder or granulate.

3. The cell culture medium according to claim 1, wherein the iron citrate diphosphate complex is present in dissolved form and the cell culture medium is an aqueous solution.

4. The cell culture medium according to claim 1, wherein the cell culture medium
i) is free of at least one serum component; and/or
ii) comprises a serum substitute; and/or
iii) comprises growth factors; and/or
iv) is free of animal or human components; and/or
v) is protein-free; and/or
vi) is hydrolyzate-free; and/or
vii) is chemically-defined.

5. The cell culture medium according to claim 1, wherein the cell culture medium
i) comprises one or more amino acids; and/or
ii) comprises one or more lipid precursors; and/or
iii) comprises one or more carboxylic acids having at least six carbon atoms or salts thereof; and/or
iv) comprises one or more carboxylic acids having fewer than six carbon atoms; and/or
v) comprises one or more nucleosides, or salts thereof; and/or
vi) comprises one or more carbohydrates.

6. The cell culture medium according to claim 1, wherein the cell culture medium
i) comprises one or more buffer substances; and/or
ii) comprises one or more trace elements, optionally further comprises a chelating agent; and/or
iii) comprises one or more vitamins.

7. The cell culture medium according to claim 1, wherein the cell culture medium comprises no iron salt.

8. The cell culture medium according to claim 1, wherein the cell culture medium comprises no iron citrate salt or iron diphosphate salt.

9. The cell culture medium according to claim 1, wherein the cell culture medium comprises a cell culture medium selected from the group consisting of DMEM, DMEM/F12 Media, Ham's F-10 Media, Ham's F-12 Media, Medium 199, MEM, RPMI 1640 Medium, ISF-1, Octomed, Ames' Medium, BGJb Medium, optionally in the Fitton-Jackson Modification, Click's Medium, CMRL-1066 Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E, combinations thereof, and modifications thereof.

10. A method for cultivating cells, comprising:
a) providing a cell culture medium in an aqueous solution, wherein the dissolved cell culture medium comprises an iron citrate diphosphate complex in an amount that an iron concentration of the cell culture medium set via the iron citrate diphosphate complex is in the range from 80 µM to 5800 µM, wherein the iron citrate diphosphate complex is an iron citrate diphosphate complex; and
b) propagating or maintaining at least one cell in the aqueous solution of the cell culture medium.

11. The method according to claim 10, wherein the cell is a cell of a primary cell line or a continuous cell line.

12. The method according to claim 10, wherein the cell is selected from the group consisting of mammalian cell, bird cell, and insect cell.

13. The method according to claim 12, wherein the mammalian cell is selected from the group consisting of CHO, NS0, SP2/0, hybridoma, HEK293, PERC-6, BHK-21 and Vero-76.

14. The method according to claim 10, further comprising introducing a nucleic acid into the at least one cell, wherein the nucleic acid causes a constitutive or induced production of at least one recombinant protein, to produce at least one recombinant protein in a cell culture.

\* \* \* \* \*